(12) United States Patent
Rigola et al.

(10) Patent No.: US 11,950,554 B2
(45) Date of Patent: Apr. 9, 2024

(54) QTLS FOR POWDERY MILDEW RESISTANCE IN MELON

(71) Applicant: Keygene N.V., Wageningen (NL)

(72) Inventors: Diana Rigola, Wageningen (NL); René Johannes Maria Hofstede, Wageningen (NL); Magdalena Barbara Lastdrager, Wageningen (NL); Jamila Maguy Chaïb, Wageningen (NL)

(73) Assignee: KEYGENE N.V., Wageningen (NL)

( * ) Notice: Subject to any disclaimer, the term of this patent is extended or adjusted under 35 U.S.C. 154(b) by 0 days.

(21) Appl. No.: 17/984,938

(22) Filed: Nov. 10, 2022

(65) Prior Publication Data

US 2023/0304030 A1 Sep. 28, 2023

Related U.S. Application Data

(63) Continuation of application No. 17/037,506, filed on Sep. 29, 2020, now Pat. No. 11,519,003, which is a continuation of application No. PCT/EP2019/058155, filed on Apr. 1, 2019.

(30) Foreign Application Priority Data

Mar. 30, 2018 (EP) .................................. 18165317

(51) Int. Cl.
| | |
|---|---|
| *A01H 1/04* | (2006.01) |
| *A01H 5/08* | (2018.01) |
| *C12N 15/82* | (2006.01) |
| *C12Q 1/6895* | (2018.01) |

(52) U.S. Cl.
CPC ............... *A01H 1/045* (2021.01); *A01H 5/08* (2013.01); *C12N 15/8282* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| | | |
|---|---|---|
| 5,591,616 A | 1/1997 | Hiei et al. |
| 2002/0138879 A1 | 9/2002 | Cai et al. |
| 2018/0325057 A1* | 11/2018 | Kosugi ................. A01H 1/045 |

FOREIGN PATENT DOCUMENTS

| | | |
|---|---|---|
| WO | WO-95/06722 | 3/1995 |
| WO | WO-2017/081876 A1 | 5/2017 |

OTHER PUBLICATIONS

Argyris et al., "Use of targeted SNP selection for an improved anchoring of the melon (*Cucumis melo* L.) scaffold genome assembly." BMC Genomics, 2015, 16:4, 14 pages.
Fukino et al., "Identification of QTLs for resistance to powdery mildew and SSR markers diagnostic for powdery mildew resistence genes in melon (*Cucumis melo* L.)", Theor Appl Genet, Sep. 17, 2008, pp. 165-175 (11 pages).
International Search Report for PCT/EP2019/058155 dated May 14, 2019 (6 pages).
Li et al., "Mapping of powdery mildew resistance genes in melon (*Cucumis melo* L.) by bulked segregant analysis", Scientia Horticulturae, Apr. 4, 2017 (8 pages).
Natarajan et al., "Whole Genome Re-Sequencing and Characterization of Powdery Mildew Disease-Associated Allelic Variation in Melon", PLOS ONE, Jun. 16, 2016 (19 pages).
Sakata et al., "QTL analysis of powdery mildew resistance in cucumber (*Cucumis sativas* L.)", Theor Appl Genet, 2006, pp. 243-250 (8 pages).
Wang et al., "Mapping quantitative trait loci for fruit traits and powdery mildew resistence in melon (*Cucumis melo*)," Botanical Studies, 2016, 57:19, 12 pages.
Yuste-Lisbona et al., "Genetic linkage map of melon (*Cucumis melo* L.) and localization of a major QTL for powdery mildew resistance", Mol Breeding, 2010, pp. 181-192 (12 pages).

* cited by examiner

*Primary Examiner* — Brent T Page
(74) *Attorney, Agent, or Firm* — Sunit Talapatra; Foley & Lardner LLP

(57) ABSTRACT

The present invention relates to genetic elements comprising powdery mildew-conferring QTLs derived from a plant of the species *Cucumis melo*, or powdery mildew-conferring part or variant thereof. The invention also relates to markers for identification of said QTLs, use thereof and methods for producing plants with increased resistance to powdery mildew and the plants thus obtained.

13 Claims, 2 Drawing Sheets

Specification includes a Sequence Listing.

SEQUENCE LISTING

```
Sequence total quantity: 16
SEQ ID NO: 1            moltype = DNA   length = 45
FEATURE                 Location/Qualifiers
source                  1..45
                        mol_type = unassigned DNA
                        organism = Cucumis melo
SEQUENCE: 1
aaataccaga caagatatca tcgccatgat tggccttcct tctgc               45

SEQ ID NO: 2            moltype = DNA   length = 45
FEATURE                 Location/Qualifiers
source                  1..45
                        mol_type = unassigned DNA
                        organism = Cucumis melo
SEQUENCE: 2
tatctctata tagaaaaact cgaaccttat gctcatgtgt gaggg               45
```

| SEQ ID NO: 3 | moltype = DNA length = 45 |
|---|---|
| FEATURE | Location/Qualifiers |
| source | 1..45 |
| | mol_type = unassigned DNA |
| | organism = Cucumis melo |

SEQUENCE: 3
gctcaattat ttcatatttt agttagctta attcaagtaa tctaa          45

| SEQ ID NO: 4 | moltype = DNA length = 45 |
|---|---|
| FEATURE | Location/Qualifiers |
| source | 1..45 |
| | mol_type = unassigned DNA |
| | organism = Cucumis melo |

SEQUENCE: 4
ctgtatcaaa ccactgtcgt caccgttttg gagcttatga ttgag          45

| SEQ ID NO: 5 | moltype = DNA length = 45 |
|---|---|
| FEATURE | Location/Qualifiers |
| source | 1..45 |
| | mol_type = unassigned DNA |
| | organism = Cucumis melo |

SEQUENCE: 5
taattgatcg atcaagcagc cctagcaaga agttgaagtt gatca          45

| SEQ ID NO: 6 | moltype = DNA length = 45 |
|---|---|
| FEATURE | Location/Qualifiers |
| source | 1..45 |
| | mol_type = unassigned DNA |
| | organism = Cucumis melo |

SEQUENCE: 6
tattaccgat agcatgcaaa tctgatctct tttctttgct cattt          45

| SEQ ID NO: 7 | moltype = DNA length = 45 |
|---|---|
| FEATURE | Location/Qualifiers |
| source | 1..45 |
| | mol_type = unassigned DNA |
| | organism = Cucumis melo |

SEQUENCE: 7
tctaattttc accatttttgc cgcttcctcc tctgagccta aaggt          45

| SEQ ID NO: 8 | moltype = DNA length = 45 |
|---|---|
| FEATURE | Location/Qualifiers |
| source | 1..45 |
| | mol_type = unassigned DNA |
| | organism = Cucumis melo |

SEQUENCE: 8
tgaagttact tcgagtgtgt atgtctatga actgttcaat gagga          45

| SEQ ID NO: 9 | moltype = DNA length = 45 |
|---|---|
| FEATURE | Location/Qualifiers |
| source | 1..45 |
| | mol_type = unassigned DNA |
| | organism = Cucumis melo |

SEQUENCE: 9
aaataccaga caagatatca tcaccatgat tggccttcct tctgc          45

| SEQ ID NO: 10 | moltype = DNA length = 45 |
|---|---|
| FEATURE | Location/Qualifiers |
| source | 1..45 |
| | mol_type = unassigned DNA |
| | organism = Cucumis melo |

SEQUENCE: 10
tatctctata tagaaaaact cggaccttat gctcatgtgt gaggg          45

| SEQ ID NO: 11 | moltype = DNA length = 45 |
|---|---|
| FEATURE | Location/Qualifiers |
| source | 1..45 |
| | mol_type = unassigned DNA |
| | organism = Cucumis melo |

SEQUENCE: 11
gctcaattat ttcatatttt agctagctta attcaagtaa tctaa          45

| SEQ ID NO: 12 | moltype = DNA length = 45 |
|---|---|
| FEATURE | Location/Qualifiers |
| source | 1..45 |
| | mol_type = unassigned DNA |
| | organism = Cucumis melo |

SEQUENCE: 12

```
ctgtatcaaa ccactgtcgt catcgttttg gagcttatga ttgag            45

SEQ ID NO: 13           moltype = DNA   length = 45
FEATURE                 Location/Qualifiers
source                  1..45
                        mol_type = unassigned DNA
                        organism = Cucumis melo
SEQUENCE: 13
taattgatcg atcaagcagc ccgagcaaga agttgaagtt gatca            45

SEQ ID NO: 14           moltype = DNA   length = 45
FEATURE                 Location/Qualifiers
source                  1..45
                        mol_type = unassigned DNA
                        organism = Cucumis melo
SEQUENCE: 14
tattaccgat agcatgcaaa tccgatctct tttctttgct cattt            45

SEQ ID NO: 15           moltype = DNA   length = 45
FEATURE                 Location/Qualifiers
source                  1..45
                        mol_type = unassigned DNA
                        organism = Cucumis melo
SEQUENCE: 15
tctaattttc accattttgc cgattcctcc tctgagccta aaggt            45

SEQ ID NO: 16           moltype = DNA   length = 45
FEATURE                 Location/Qualifiers
source                  1..45
                        mol_type = unassigned DNA
                        organism = Cucumis melo
SEQUENCE: 16
tgaagttact tcgagtgtgt atatctatga actgttcaat gagga            45
```

QTLS FOR POWDERY MILDEW RESISTANCE IN MELON

CROSS-REFERENCE TO RELATED APPLICATIONS

This application is a continuation of U.S. patent application Ser. No. 17/037,506, filed Sep. 29, 2020, which application is a continuation of International Application No. PCT/EP2019/058155 filed Apr. 1, 2019, which claims the benefit of and priority to European Application No. 18165317.1 filed Mar. 30, 2018, both of which are hereby incorporated by reference herein in their entireties.

SEQUENCE LISTING

The instant application contains a Sequence Listing which is being submitted in XML format electronically and is hereby incorporated by reference in its entirety. Said XML copy, created on May 24, 2023, is named 085342-3701_SL.xml and is 15,451 bytes.

BACKGROUND

Melons are annual, herbaceous, flowering plant species which were domesticated early and have been cultivated for thousands of years in African and Asian countries. They are presently cultivated worldwide and provide delicious and highly nutritious fruits. Melons are typically consumed fresh, in salads or prepared into desserts, appetizers, or drinks, for which they can be combined with a variety of other ingredients.

Melon plants of the species *Cucumis melo* belong to the cucurbit family, scientifically called the Cucurbitaceae. Together with the important food crop cucumber, *Cucumis sativus*, *Cucumis melo* belongs to the genus *Cucumis*. The species *Cucumis melo* has taxonomically been classified, for example using a division into subspecies *melo* and *agrestis* with further classification into varieties, wherein basically all cultivated melons belong to the ssp. *melo*.

Melon is a diploid plant species with twelve pairs of chromosomes. Melon plants of the species *Cucumis melo* are principle self-pollinators but cross pollination also occurs frequently. Like in most crops, commercial melon cultivars were initially open-pollinated, but nowadays many high yielding hybrid varieties are available.

Melon production is most successful in a climate with a long warm sunny season that is relatively dry. Melons are grown throughout the world. Cultivation is both in open field as well as under protected circumstances (e.g. greenhouses). Since basically all cultivated melon belong to the ssp. *Melo*, no crossing barriers exist and combinations between different types of melon have been and are subject to breeding programs.

Several pests and diseases can affect melon production, including several viruses, bacterial and fungal diseases. Typical diseases caused by viral infection include infection by Melon Necrotic Spot Virus (MNSV), Watermelon Mosaic Virus (WMV), and Cucurbit Yellow Stunting Disorder Virus (CYSDV). Typical diseases caused by fungal infection include downy mildew, powdery mildew, and gummy stem blight.

Of the above-mentioned diseases powdery mildew (hereinafter also referred to as "PM") is one of the main fungal diseases in *Cucumis*, including *Cucumis melo*. This disease is observed both in the field and greenhouse.

Powdery mildew can easily been identified as the symptoms of the fungal infection are quite distinctive. Plants that are infected display white powdery spots on the leaves and stems. In particular the lower leaves are affected, but the mildew may appear on any part of the plant that is exposed above ground. As the disease progresses the powdery spots increase in size and get thicker as massive numbers of spores form. In time the mildew spreads over the plant and may infect the stem and even the fruits. Severely affected plant parts, in particular the leaves, can become dry and brittle, or can wither and die. As a consequence of the fungal infection the melon fruits are frequently observed to be smaller in size, fewer in number, less able to be stored, sun scalded, incompletely ripe, and to have poor flavor. It has also been suggested that powdery mildew may predispose plants to be more vulnerable to other pathogens. Eventually, the plant can die.

Powdery mildew develops quickly under favorable conditions because the length of time between infection and symptom appearance is usually only 3 to 7 days and a large number of conidia (asexual spore) can be produced in a short time. Favorable conditions include dense plant growth and low light intensity. High relative humidity is favorable for infection and conidial survival whereas dryness is favorable for colonization, sporulation, and dispersal. Powdery mildew development is arrested when daytime temperatures are at least 38 degrees Celsius.

Fungicide treatments may be used to prevent (further) development of powdery mildew on melon. For example, sulfur is a treatment that has been used for hundreds of years. However, in order to obtain adequate control, fungicide is needed on the undersurface of leaves and on leaves low in the plant canopy because the fungus develops best on these surfaces and weekly spraying programs are typically required. Development of fungicide resistance and consequent control failure is always a concern with mobile fungicides. Indeed strains of the powdery mildew fungus resistant (insensitive) to such fungicides have been found.

Powdery mildew diseases are generally caused by different species of ascomycete fungi of the order Erysiphales. Two causal agents of powdery mildew on melon have been identified: *Podosphaera xanthii* (also designated as *Oidium erysiphoides*; formerly *Sphaerotheca fuliginea*) and *Golovinomyces cichoracearum* (also designated as *Oidium chrysanthemi*; formerly *Erysiphe cichoracearum*).

Plants of the species *Cucumis melo* that display resistance to powdery mildew has been described. For example melon (*Cucumis melo* L.) PI 313970 exhibited resistance to powdery mildew incited by *Sphaerotheca fuliginea* (Schlecht ex Fr.) Poll. race 2. Also PI 124111 was resistant in a greenhouse to race 2 (McCreight (2001) Cucurbit Genetics Cooperative Report 24:22; McCreight et al (2011) HortScience 46(6):838-840). Also Pitrat et al. described inheritable resistance to powdery mildew in the melone line '90625' (Cucurbitaceae 2008, Proceedings of the IXth EUCARPIA meeting on genetics and breeding of Cucurbitaceae (Pitrat M, ed), INRA, Avignon (France), May 21-24th, 2008, pp 135-142). International patent application WO2012/116938 discloses powdery mildew resistance providing genes of the *Cucumis* family, and especially *Cucumis melo*, wherein said resistance is provided by impairment of the genes.

As already discussed above, fungicide treatments to control powdery mildew is rather complex and negatively affect the environment and may cause the development of powdery mildew fungus resistant (insensitive) to such fungicides. Therefor, and considering the economic importance of *Cucumis* plant species, in particular *Cucumis melo*, there is a continued need in the art to provide non-chemical alternatives to overcome powdery mildew in *Cucumis* plant species, in particular there is a continued need in the art for powdery mildew resistance plants, genetic elements comprising powdery mildew-conferring QTLs and markers for identification of said QTLs, use thereof and methods for producing plants with increased resistance to powdery mildew.

In view of the above need in the art, it is an object of the present invention, amongst other objects, to meet this need. Accordingly, the technical problem underlying the present invention can been seen in the provision of such products, compositions, methods and uses for complying with any of the aforementioned needs. The technical problem is solved by the embodiments characterized in the claims and herein below.
Description

BRIEF DESCRIPTION OF DRAWINGS

Embodiments of the invention are further described hereinafter with reference to the accompanying drawings, in which.

DEFINITIONS

Figure 1:
FIG. 1: Illustration of leaf disc appearance with concomitant resistance scores.

A portion of this disclosure contains material that is subject to copyright protection (such as, but not limited to, diagrams, device photographs, or any other aspects of this submission for which copyright protection is or may be available in any jurisdiction). The copyright owner has no objection to the facsimile reproduction by anyone of the patent document or patent disclosure, as it appears in the Patent Office patent file or records, but otherwise reserves all copyright rights whatsoever.

Various terms relating to the methods, compositions, uses and other aspects of the present invention are used throughout the specification and claims. Such terms are to be given their ordinary meaning in the art to which the invention pertains, unless otherwise indicated. Other specifically defined terms are to be construed in a manner consistent with the definition provided herein. Although any methods and materials similar or equivalent to those described herein can be used in the practice for testing of the present invention, the preferred materials and methods are described herein.

For purposes of the present invention, the following terms are defined below.

As used herein, the singular forms "a," "an" and "the" include plural referents unless the context clearly dictates otherwise. For example, a method for administrating a drug includes the administrating of a plurality of molecules (e.g. 10's, 100's, 1000's, 10's of thousands, 100's of thousands, millions, or more molecules).

As used herein, the term "and/or" indicates that one or more of the stated cases may occur, alone or in combination with at least one of the stated cases, up to with all of the stated cases. For instance, the wording "QTL-VI and/or QTL-XII" indicates "QTL-VI, QTL-XII or a combination of QTL-VI and QTL-XII".

As used herein, "to comprise" and its conjugations is used in its non-limiting sense to mean that items following the word are included, but items not specifically mentioned are not excluded. It also encompasses the more limiting "to consist or."

As used herein, the term "construct" or "nucleic acid construct" or "vector" refers to a man-made nucleic acid molecule resulting from the use of recombinant DNA technology and which may be used to deliver exogenous DNA into a host cell, often with the purpose of expression in the host cell of a DNA region comprised on the construct. The vector backbone may for example be a binary or superbinary vector (see e.g. U.S. Pat. No. 5,591,616, US 2002138879 and WO95/06722), a co-integrate vector or a T-DNA vector, as known in the art and as described elsewhere herein, into which a chimeric gene is integrated or, if a suitable transcription regulatory sequence is already present, only a desired nucleic acid sequence (e.g. a coding sequence, an antisense or an inverted repeat sequence) is integrated downstream of the transcription regulatory sequence. The vector backbone of a construct may for example be a plasmid into which a (chimeric) gene is integrated or, if a suitable transcription regulatory sequence is already present, only a desired nucleic acid (e.g. a coding part) is integrated. Vectors may comprise further genetic elements to facilitate their use in molecular cloning, such as e.g. selectable markers, multiple cloning sites and the like.

"Sequence identity" and "sequence similarity" can be determined by alignment of two peptide or two nucleotide sequences using global or local alignment algorithms, depending on the length of the two sequences. Sequences of similar lengths are preferably aligned using a global alignment algorithms (e.g. Needleman Wunsch) which aligns the sequences optimally over the entire length, while sequences of substantially different lengths are preferably aligned using a local alignment algorithm (e.g. Smith Waterman). Sequences may then be referred to as "substantially identical" or "essentially similar" when they (when optimally aligned by for example the programs GAP or BESTFIT using default parameters) share at least a certain minimal percentage of sequence identity (as defined below). GAP uses the Needleman and Wunsch global alignment algorithm to align two sequences over their entire length (full length), maximizing the number of matches and minimizing the number of gaps. A global alignment is suitably used to determine sequence identity when the two sequences have similar lengths. Generally, the GAP default parameters are used, with a gap creation penalty=50 (nucleotides)/8 (proteins) and gap extension penalty=3 (nucleotides)/2 (proteins). For nucleotides the default scoring matrix used is nwsgapdna and for proteins the default scoring matrix is Blosum62 (Henikoff & Henikoff, 1992, PNAS 89, 915-919). Sequence alignments and scores for percentage sequence identity may be determined using computer programs, such as the GCG Wisconsin Package, Version 10.3, available from Accelrys Inc., 9685 Scranton Road, San Diego, CA 92121-3752 USA, or using open source software, such as the program "needle" (using the global Needleman Wunsch algorithm) or "water" (using the local Smith Waterman algorithm) in EmbossWIN version 2.10.0, using the same parameters as for GAP above, or using the default settings (both for 'needle' and for 'water' and both for protein and for DNA alignments, the default Gap opening penalty is 10.0 and the default gap extension penalty is 0.5; default scoring matrices are Blossum62 for proteins and DNAFull for DNA). When sequences have a substantially different overall lengths, local alignments, such as those using the Smith Waterman algorithm, are preferred. Alternatively percentage similarity or identity may be determined by searching against public databases, using algorithms such as FASTA, BLAST, etc. Thus, the nucleic acid and protein sequences of the present invention can further be used as a "query sequence" to perform a search against public databases to, for example, identify other family members or related sequences. Such searches can be performed using the BLASTn and BLASTx programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to oxidoreductase nucleic acid molecules of the invention. BLAST protein searches can be performed with the BLASTx program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., BLASTx and BLASTn) can be used. See the homepage of the National Center for Biotechnology Information at http://www.ncbi.nlm.nih.gov/.

As used herein, the term "linkage group" refers to all of the genes or genetic traits that are located on the same chromosome. Within the linkage group, those loci that are close enough together will exhibit linkage in genetic crosses. Since the probability of crossover increases with the physical distance between genes on a chromosome, genes whose locations are far removed from each other within a linkage group may not exhibit any detectable linkage in direct genetic tests. The term "linkage group" is mostly used to refer to genetic loci that exhibit linked behavior in genetic systems where chromosomal assignments have not yet been made.

As used herein, the term "molecular marker" or "marker" refers to an indicator which defines a specific genetic and chromosomal location, i.e. marks a particular position on the chromosome. Well-known examples known to the skilled person include amplified fragment length polymorphism (AFLP) markers, restriction fragment length polymorphism (RFLP) markers, single nucleotide polymorphisms (SNPs), sequence-characterized amplified regions (SCARs), cleaved amplified polymorphic sequence (CAPS) markers or isozyme markers or combinations of the markers described herein. If a molecular marker is tightly linked to a QTL it "marks" the DNA on which the QTL is found and can therefore be used in a (molecular) marker assays to select for or against the presence of the QTL, e.g. in marker assisted breeding/selection (MAS) methods. A "(molecular) marker linked to a QTL" or "(molecular) marker for identification of a QTL" may thus refer to, for example, SNPs or any other type of marker used in the field, and that is linked to the QTL. In other words, "A marker for identification of a QTL that leads to resistance to powdery mildew" refers to a marker that may be used to positively identify a QTL that is associated with powdery mildew resistance.

As used herein, the term "melon" refers to the species Cucumis melo L. Melons or 'muskmelons', Cucumis melo, can be classified into: C. melo cantalupensis, C. melo inodorous and C. melo reticulatus The term includes wild accessions and cultivars. Cucumis melo is by some considered to consist of the subspecies Cucumis melo subsp. agrestis and Cucumis melo subsp. melo. Melon and the wild relatives of melon is/are diploid and has/have 12 pairs of homologous chromosomes, numbered 1 to 12. "Melon chromosome 6" refers to the C. melo chromosome 6 (Argyis et al. BMC Genomics (2015) 16:4).

Reference genome as used herein is the public pseudomolecules sequence of DHL92 Melon line (WGS v3.5.1 as described in Jason M Argyris et al. Use of targeted SNP selection for an improved anchoring of the melon (Cucumis melo L.) scaffold genome assembly. BMC Genomics. 2015 Jan. 22; 16:4; http://www.icug org/organ ism/3).

Herein melon chromosome 6 is equivalent to LG VI or Linkage Group VI and pseudomolecule 6. Herein melon chromosome 12 is equivalent to LG XII or Linkage Group XII and pseudomolecule 12.

As used herein "cultivar" denotes a plant having a biological status that is not "wild" status. The "wild" status indicates the original or natural state of a plant or accession. Examples of cultivars include Cucumis melo subsp. melo cultivars from several botanical varieties, e.g. Vedrantais (var. cantalupensis), Piel de Sapo (var. inodorus) and Dulce (var. reticulatus). Therefore, a plant of the present in invention is preferably a plant of the melon botanical varieties Vedrantais (var. cantalupensis), Piel de Sapo (var. inodorus) and Dulce (var. reticulatus). Accordingly "cultivar" also indicates a group of similar plants that by structural or genetic features can be distinguished from other cultivated varieties within the same species. A plant of the present invention is preferably not a Cucumis melo var. agrestis plant, preferably not Melon accession PI 313970.

The term "powdery mildew" is used herein in its common and well-known meaning in the art. Powdery mildew is caused by well-known powdery mildew causing agents, for example Podosphaera xanthii and/or Golovinomyces cichoracearum. As used herein, the terms "resistant" and "resistance" in the context as used herein encompass both partial and full resistance to infection, in particular to infection by the powdery mildew causing agent. Specifically, "resistance" refers to the ability of a plant to restrict the growth and development of a specified pest or pathogen and/or the damage they cause when compared to susceptible plant under similar environmental conditions and pest or pathogen pressure. Resistant varieties may exhibit some disease symptoms under heavy pest or pathogen pressure. Susceptibility refers to the inability of a plant to restrict the growth and development of a specified pest or pathogen. Accordingly, the term "powdery mildew resistant" or "powdery mildew resistance" refers to partial of full resistance to infection by a powdery mildew causing agent, for example Podosphaera xanthii and/or Golovinomyces cichoracearum. The phenotypic presence of the resistance to powdery mildew can be tested using a bio-assay, such as described herein in detail in the Example section. A powdery mildew-susceptible melon plant may be non-resistant or have only low levels of resistance to infection by said powdery mildew causing agent. A QTL or combination of QTLs leading to resistance, or leading to increased resistance, is to be understood herein as a QTL or combination of QTLs that confer(s) PM resistance to a test plant as compared to a control plant, wherein the control plant preferably only differs from the test plant in that it does not bear said QTL or said combination of QTLs, preferably as quantified using the bio-assay as detailed herein in the Example section, and preferably wherein said test plant scores at least 1, 1.5, 2, 2.5, 3, 3.5 or at least 4 points lower in resistance score as compared to the control plant.

As used herein, the term "heterozygous" means the genetic condition wherein different alleles reside at corresponding loci on homologous chromosomes. As used herein, the term "homozygous" means a genetic condition wherein identical alleles reside at corresponding loci on homologous chromosomes.

As used herein, the terms "introgression", "introgressed" and "introgressing" relate to a process whereby genes of one species, variety or cultivar are moved into the genome of another species, variety or cultivar, by crossing those species. The process may optionally include backcrossing to the recurrent parent.

As used herein, the term "marker assisted selection (MAS)" refers to a process whereby plants are screened for the presence and/or absence of one or more genetic and/or phenotypic markers in order to accelerate the transfer of the DNA region comprising the marker (and optionally lacking flanking regions) into an (elite) breeding line. In other words, "MAS" is a process of using the presence of molecular markers, which are genetically linked to a particular locus or to a particular chromosome region (e.g. introgression fragment), to select plants for the presence of the specific locus or region (introgression fragment). For example, a molecular marker genetically linked to a powdery mildew resistance QTL, can be used to detect and/or select melon plants comprising the powdery mildew resistance QTL.

As used herein, the term "molecular maker assay" (or test) refers to any (DNA based) assay that indicates (directly or indirectly) the presence or absence of an allele of interest, e.g. a QTL, in a plant or plant part. Such tests are well-known to the skilled person As used herein, the term "nucleic acid" refers to any polymer or oligomer of pyrimidine and purine bases, preferably cytosine, thymine, and uracil, and adenine and guanine, respectively (See Albert L. Lehninger, *Principles of Biochemistry*, at 793-800 (Worth Pub. 1982) which is herein incorporated by reference in its entirety for all purposes). The polymers or oligomers (polynucleotide or oligonucleotide) may be heterogeneous or homogenous in composition, and may be isolated from naturally occurring sources or may be artificially or synthetically produced. The nucleic acids may be DNA or RNA, or a mixture thereof, and may exist permanently or transitionally in single-stranded or double-stranded form, including homoduplex, heteroduplex, and hybrid states. As used herein, the term "isolated nucleic acid" refers to a nucleic acid which is substantially separated from other cellular components which naturally accompany the nucleic acid molecule. The term embraces a nucleic acid (sequence) which has been removed from its naturally occurring environment and includes recombinant or cloned nucleic acid isolates and chemically synthesized analogs or analogs biologically synthesized by heterologous systems.

As used herein, the term "phenotype" refers to the observable characteristics or traits of an organism such as its morphology, development, biochemical or physiological properties, phenology, behavior, and products of behavior. Phenotypes result from the expression of the genes, or lack thereof, as well as the influence of environmental factors and the interactions between the two. Although a phenotype is the ensemble of observable characteristics displayed by an organism, the word phenome is sometimes used to refer to a collection of traits and their simultaneous study is referred to as phenomics. For example, one phenotype is powdery mildew resistance, whereas another phenotype is powdery mildew susceptibility.

"Promoter" refers to a nucleic acid fragment that functions to control the transcription of one or more nucleic acids. A promoter fragment is, located upstream (5') with respect to the direction of transcription of the transcription initiation site of the gene, and is structurally identified by the presence of a binding site for DNA-dependent RNA polymerase, transcription initiation site(s) and can further comprise any other DNA sequences, including, but not limited to transcription factor binding sites, repressor and activator protein binding sites, and any other sequences of nucleotides known to one of skill in the art to act directly or indirectly to regulate the amount of transcription from the promoter. Optionally the term "promoter" may also include the 5' UTR region (5' Untranslated Region) (e.g. the promoter may herein include one or more parts upstream of the translation initiation codon of transcribed region, as this region may have a role in regulating transcription and/or translation). A "constitutive" promoter is a promoter that is active in most tissues under most physiological and developmental conditions. An "inducible" promoter is a promoter that is physiologically (e.g. by external application of certain compounds) or developmentally regulated. A "tissue specific" promoter is only active in specific types of tissues or cells.

As used herein, the term "Quantitative Trait Locus" or "QTL" is used in its meaning as recognized by the skilled person. The term "QTL associated with powdery mildew resistance (in *Cucumis melo*)" or "QTL, when present in the genome of a plant of the plant species *Cucumis melo*, leads to resistance to powdery mildew" refers to a region located on a particular chromosome of a plant of the species *Cucumis melo* that is associated with at least one gene that confers powdery mildew-resistance, or at least a regulatory region of a chromosome that controls the expression of one or more genes involved in powdery mildew resistance. A QTL may for instance comprise one or more genes of which the products confer the resistance. A QTL may for instance also comprise one or more impaired genes, i.e. mutated genes, the impairment of said gene causing resistance to powdery mildew (i.e. as compared to e.g. a wild-type, powdery mildew susceptibility-conferring gene). Such mutation can through different mechanisms results in impairment. For example, mutations in protein encoding DNA sequences may lead to mutated, truncated or non-functional proteins. Mutations in non-coding DNA sequences may cause alternative splicing, translation or protein trafficking. Alternatively, a mutation resulting in an altered transcriptional activity of a gene may results in low levels, or absence, of proteins. Alternatively, a QTL may comprise regulatory genes or sequences of which the products influence the expression of genes on other loci in the genome, thereby conferring powdery mildew resistance.

As used herein "transferring of nucleic acid" relates to the transfer of an isolated nucleic acid, for example comprised in a nucleic acid construct or vector, to an organism, usually into the DNA, usually the chromosomal DNA or genome, of said organism.

DETAILED DESCRIPTION

It is contemplated that any method, use or composition described herein can be implemented with respect to any other method, use or composition described herein. Embodiments discussed in the context of methods, use and/or compositions of the invention may be employed with respect to any other method, use or composition described herein. Thus, an embodiment pertaining to one method, use or composition may be applied to other methods, uses and compositions of the invention as well.

As embodied and broadly described herein, the present invention is directed to the surprising identification of a hitherto unknown genetic region linked to powdery mildew resistance in *Cucumis melo*. The quantitative trait locus (QTL) identified by the current inventors and that is linked to powdery mildew resistance, in other words, the powdery mildew conferring quantitative trait locus, is named herein "QTL-VI". QTL-VI was identified on chromosome 6 (Argyris et al. BMC Genomics (2015) 16:4;) in melon plant representative seed deposited with the NCIMB under deposit number NCIMB 42991 (deposit date: 28 Mar. 2018, depositor: Vilmorin & Cie, 4 quai de la Megisserie, 75001 Paris, France), between the positions that can be identified using the corresponding markers as described herein below (i.e. within the chromosomal region delimited by SEQ ID NO: 1 and SEQ ID NO:2, preferably within the chromosomal region delimited by SEQ ID NO: 3 and SEQ ID NO: 4). The current inventors have identified hitherto unknown molecular markers, e.g. SNP markers, that can be used for the identification of QTL-VI, i.e. that can be used for the identification of the powdery mildew resistance QTL QTL-VI.

Therefore, an aspect of the current invention is the identification of QTL-VI as a QTL involved in powdery mildew resistance, i.e. leading to increased powdery mildew resistance when present in the genome of a plant of the species Cucumis melo, preferably when present in homozygous form. A further aspect is the finding of marker(s) that can be used to alone or in combination for the identification of QTL-VI.

On top of that, the current inventors have identified a second genetic region linked to powdery mildew resistance in Cucumis melo. The second quantitative trait locus (QTL) identified, and that is linked to powdery mildew resistance, is named herein "QTL-XII". QTL-XII was identified on chromosome 12, (Argyis et al. BMC Genomics (2015) 16:4) in melon plant representative seed deposited with the NCIMB under deposit number NCIMB 42991, between the positions that can be identified using the corresponding markers as described herein below (i.e. within the chromosomal region delimited by SEQ ID NO: 5 and SEQ ID NO: 6, preferably within the chromosomal region delimited by SEQ ID NO: 7 and SEQ ID NO: 8). The current inventors have identified hitherto unknown molecular markers, e.g. SNP markers, that can be used for the identification of QTL-XII, i.e. that can be used for the identification of the second powdery mildew resistance QTL QTL-XII.

Therefore, an aspect of the current invention is the identification QTL-XII as a QTL involved in powdery mildew resistance, i.e. leading to powdery mildew resistance when present in the genome of a plant of the species Cucumis melo, preferably when present in homozygous form. A further aspect is the finding of marker(s) that can be used to alone or in combination for the identification of QTL-XII.

A further aspect of the current invention is the identification the combination of QTL-VI and QTL-XII as QTLs that are together involved in powdery mildew resistance, i.e. leading to powdery mildew resistance when present in the genome of a plant of the species Cucumis melo, preferably when present in homozygous form. A further aspect is the finding of marker(s) that can be used in combination for the identification of both QTL-VI and QTL-XII.

This and other aspects of the current invention are also exemplified in the accompanying Example(s).

Therefore, in an embodiment the invention relates to a marker for identification of QTL-VI, wherein said QTL-VI, when present in the genome of a plant of the species Cucumis melo, leads to increased resistance to powdery mildew, wherein the marker is detectable by a molecular marker assay and is selected from the group consisting of:
  'G' on position 23 of SEQ ID NO: 1 corresponding to the physical position 5,330,645 bp of the public melon genome;
  'A' on position 23 of SEQ ID NO: 2 corresponding to the physical position 6,006,456 bp of the public melon genome;
  'T' on position 23 of SEQ ID NO: 3 corresponding to the physical position 5,414,506 bp of the public melon genome; and,
  'C' on position 23 of SEQ ID NO: 4 corresponding to the physical position 5,738,920 bp of the public melon genome.

In the course of the experiments performed by the inventors, and during identification of QTL-VI on chromosome 6 as a QTL that is involved in powdery mildew resistance, in particular in plants of the species Cucumis melo, genotyping resulted in mapping of various SNP markers that can be used for identification of QTL-VI.

When these markers are positioned on the public melon genome for Cucumis melo, based on the DHL92 Melon line (Reference genome is the public pseudomolecules sequence of DHL92 Melon line (Jason M Argyris et al. Use of targeted SNP selection for an improved anchoring of the melon (Cucumis melo L., which is incorporated herein by reference) scaffold genome assembly. BMC Genomics 2015 16:4. DOI: 10.1186/s12864-014-1196-3)), the indicated marker 'G' on position 23 of SEQ ID NO: 1 corresponds to the physical position 5,330,645 bp; the indicated marker 'A' on position 23 of SEQ ID NO: 2 corresponds to the physical position 6,006,456 bp of the public melon genome; the indicated marker 'T' on position 23 of SEQ ID NO: 3 corresponds to the physical position 5,414,506 bp of the public melon genome; and the indicated marker 'C' on position 23 of SEQ ID NO: 4 corresponding to the physical position 5,738,920 bp of the public melon genome. It will be understood by the skilled person that the position of QTL-VI is also derivable from the public genome sequence and is relative to said physical positions.

The SNP markers are represented by SEQ ID Nos 1-4, and shown in Table 1. Table 1 shows the various markers for QTL-VI (resistant).

TABLE 1

Markers for the identification of QTL-VI.
Indicated are the physical position of the SNP
and the corresponding nucleotide at that position
that is linked with QTL-VI (Resistant) or not (Sensitive).

| Markers QTL-VI | Physical position of the SNP[1] | Sensitive | Resistant |
| --- | --- | --- | --- |
| >Cm_477 | 5,330,645 | A | G |
| >Cm_473 | 6,006,456 | G | A |
| Length (bp) | 675,811 | | |
| >Cm_476 | 5,414,506 | C | T |
| >Cm_374 | 5,738,920 | T | C |
| Length (bp) | 324,414 | | |

[1]Reference genome is the public pseudomolecules sequence of DHL92 Melon line (Jason M Argyris et all. Use of targeted SNP selection for an improved anchoring of the melon (Cucumis melo L.) scaffold genome assembly. BMC Genomics 2015 16:4. DOI: 10.1186/s12864-014-1196-3)

Also indicated in Table 1 are the nucleotides that are present at the same position in the plant of the species Cucumis melo not comprising QTL-VI, and as used in the accompanying Example. As will be understood by the skilled person these markers (sensitive) can be used to identify plants of the species Cucumis melo that do not comprise QTL-VI. The SNP markers are represented by SEQ ID Nos 9-12.

With respect to the markers that can be used for identification of QTL-VI, wherein said QTL-VI, when present in the genome of a plant of the species *Cucumis melo*, leads to resistance to powdery mildew, and as represented by SEQ ID Nos 1-4:

On position 23 of SEQ ID NO: 1, corresponding to the physical position 5,330,645 bp of the public melon genome, a G is present, i.e. a G is indicative for the presence of QTL-VI.

On position 23 of SEQ ID NO: 2, corresponding to the physical position 6,006,456 bp of the public melon genome, an A is present, i.e. an A is indicative for the presence of QTL-VI.

On position 23 of SEQ ID NO: 3, corresponding to the physical position 5,414,506 bp of the public melon genome, a T is present, i.e. a T is indicative for the presence of QTL-VI.

On position 23 of SEQ ID NO: 4 corresponding to the physical position 5,738,920 bp of the public melon genome, a C is present, i.e. a C is indicative for the presence of QTL-VI.

As will be understood by the skilled person, one or more of the above identified markers may be used for the identification of QTL-VI, for example as described herein. Thus, in one embodiment, the marker(s) for identification of QTL-VI is (are) one or more of (the markers represented by) the 'G' on position 23 of SEQ ID NO: 1; the 'A' on position 23 of SEQ ID NO: 2; the 'T' on position 23 of SEQ ID NO: 3 and the 'C' on position 23 of SEQ ID NO: 4. Likewise, also contemplated by the present invention are markers for identification of the absence of QTL-VI, which are one or more of (the markers represented by) a 'C', 'T' or 'A', preferably an 'A', on position 23 of SEQ ID NO: 1; a 'C', 'T' or 'G', preferably a 'G', on position 23 of SEQ ID NO: 2; a 'C', 'A' or 'G', preferably a 'C', on position 23 of SEQ ID NO: 3; a 'T', 'A' or 'G', preferably a 'T', on position 23 of SEQ ID NO: 4.

As described herein, the markers as indicated, do not only correlate to the presence of the specific phenotypic trait in the plant, they also indicate the location of the QTL-VI. In general, the location of a QTL may be indicated by a contiguous string of markers that exhibit statistical correlation to the phenotypic trait. Once a marker is found outside that string the boundaries of the QTL are set. Thus, it is also possible to indicate the location of the QTL by other markers located within that specified region. In other words, the location of QTL-VI corresponds to the chromosomal region delimited by SEQ ID NO: 1 and SEQ ID NO: 2, preferably delimited by SEQ ID NO: 3 and SEQ ID NO: 4. In Table 1 the length (bp) delimited by said SEQ ID NOs is also indicated.

The markers according to the invention are preferably markers that are detectable by molecular marker assay. Molecular marker assays are well-known to the skilled persons and include, for example, RFLP, SSR, SNP and AFLP based assays.

As will be understood by the skilled person, the marker may be of any length that is allowable by the molecular marker assay suitably used for identifying the markers disclosed herein, and therewith identifying QTL-VI. In an embodiment of the current invention, the marker for identification of QTL-VI comprises a sequence selected from the group of SEQ ID NO: 1, SEQ ID NO: 2, SEQ ID NO: 3 and SEQ ID NO: 4.

In the course of the experiments performed by the inventors, a second QTL was identified, designated QTL-XII. Said QTL-XII, positioned on chromosome 12 within the chromosomal region delimited by SEQ ID NO: 5 and SEQ ID NO: 6, preferably within the chromosomal region delimited by SEQ ID NO:7 and SEQ ID NO:7, leads, when present in the genome of a plant of the species *Cucumis melo* together with QTL-VI, to resistance to powdery mildew. Moreover, the presence of QTL-XII in a plant comprising QTL-VI leads to increased resistance to powdery mildew as compared to a control plant comprising QTL-VI while lacking QTL-XII.

Also here, further genotyping resulted in mapping of various SNP markers that can be used for identification of QTL-XII. Therefore, in an embodiment, the invention relates to a marker for identification of a QTL-XII, wherein said QTL-XII, when present in the genome of a plant of the species *Cucumis melo* together with QTL-VI, leads to resistance to powdery mildew, wherein the marker is detectable by a molecular marker assay and is selected from the group consisting of:

'T' on position 23 of SEQ ID NO: 5 corresponding to the physical position 22,675,877 bp of the public melon genome;

'T' on position 23 of SEQ ID NO: 6 corresponding to the physical position 22,923,842 bp of the public melon genome;

'C' on position 23 of SEQ ID NO: 7 corresponding to the physical position 22,781,889 bp of the public melon genome; and, 'G' on position 23 of SEQ ID NO: 8 corresponding to the physical position 22,788,588 bp of the public melon genome.

When these markers are positioned on the public melon genome for *Cucumis melo*, as described above, the indicated marker 'T' on position 23 of SEQ ID NO: 5 corresponds to the physical position 22,675,877 bp; the indicated marker 'T' on position 23 of SEQ ID NO: 6 corresponds to the physical position 22,923,842 bp of the public melon genome; the indicated marker 'C' on position 23 of SEQ ID NO: 7 corresponds to the physical position 22,781,889 bp of the public melon genome; and the indicated marker 'G' on position 23 of SEQ ID NO: 8 corresponding to the physical position 22,788,588 bp of the public melon genome. It will be understood by the skilled person that the position of QTL-XII is also derivable from the public genome sequence and is relative to said physical positons.

The SNP markers are represented by SEQ ID Nos 5-8, and shown in Table 2. Table 2 shows the various markers for QTL-XII (resistant).

TABLE 2

Markers for the identification of QTL-XII.
Indicated are the physical position of
the SNP and the corresponding nucleotide at that
position that is linked with QTL-XII (Resistant) or
not (Sensitive), and in the context of the current invention.

| Marker_QTL-XII | Physical position of the SNP[1] | Sensitive | Resistant |
|---|---|---|---|
| >Cm_382 | 22,675,877 | G | T |
| >Cm_512 | 22,923,842 | C | T |
| Length (bp) | 247,965 | | |
| >Cm_511 | 22,781,889 | A | C |
| >Cm_569 | 22,788,588 | A | G |
| Length (bp) | 6699 | | |

[1]Reference genome is the public pseudomolecules sequence of DHL92 Melon line (Jason M Argyris et all. Use of targeted SNP selection for an improved anchoring of the melon (Cucumis melo L.) scaffold genome assembly. BMC Genomics 2015 16:4. DOI: 10.1186/s12864-014-1196-3).

Also indicated in Table 2 are the nucleotides that are present at the same position in the plant of the species *Cucumis melo* not comprising QTL-XII, and as used in the accompanying Example. As will be understood by the skilled person these markers (sensitive) can be used to identify plants of the species *Cucumis melo* that do not comprise QTL-XII. The SNP markers are represented by SEQ ID NO: 13-16.

With respect to the markers that can be used for identification of QTL-XII, wherein said QTL-XII, when present in the genome of a plant of the species *Cucumis melo* together with QTL-VI, leads to resistance to powdery mildew, and as represented by SEQ ID Nos 5-8:
  On position 23 of SEQ ID NO: 5, corresponding to the physical position 22,675,877 bp of the public melon genome, a T is present, i.e. a T is indicative for the presence of QTL-XII.
  On position 23 of SEQ ID NO: 6, corresponding to the physical position 22,923,842 bp of the public melon genome, a T is present, i.e. a T is indicative for the presence of QTL-XII.
  On position 23 of SEQ ID NO: 7, corresponding to the physical position 22,781,889 bp of the public melon genome, a C is present, i.e. a C is indicative for the presence of QTL-XII.
  On position 23 of SEQ ID NO: 8 corresponding to the physical position 22,788,588 bp of the public melon genome, a G is present, i.e. a G is indicative for the presence of QTL-XII.

As will be understood by the skilled person, one or more of the above identified markers may be used for the identification of QTL-XII, for example as described herein. Thus, in one embodiment, the marker(s) for identification of QTL-XII is (are) one or more of (the markers represented by) the 'T' on position 23 of SEQ ID NO: 5; the 'T' on position 23 of SEQ ID NO: 6; the 'C' on position 23 of SEQ ID NO: 7 and the 'G' on position 23 of SEQ ID NO: 8. Likewise, also contemplated by the present invention are markers for identification of the absence of QTL-XII, which are one or more of (the markers represented by) a 'C', 'G' or 'A', preferably a 'G', on position 23 of SEQ ID NO: 5; a 'C', 'A' or 'G', preferably a 'C', on position 23 of SEQ ID NO: 6; a 'G', 'A' or 'T', preferably an 'A', on position 23 of SEQ ID NO: 7; a 'T', 'A' or 'C', preferably an 'A', on position 23 of SEQ ID NO: 8.

As described herein, the markers for QTL-XII as indicated, do not only correlate to the presence of the specific phenotypic trait in the plant, in particular when QTL-VI is comprised in the genome of the same plant of the species *Cucumis melo*, preferably in homozygous form, they also indicate the location of the QTL-XII. As will be understood by the skilled person, it is also possible to indicate the location of the QTL by other markers located within that specified region. In other words, the location of QTL-XII corresponds to the chromosomal region delimited by SEQ ID NO: 5 and SEQ ID NO: 6, preferably delimited by SEQ ID NO: 7 and SEQ ID NO: 8. In Table 2 the length (bp) delimited by said SEQ ID NOs is also indicated.

As will be understood by the skilled person, the marker for QTL-XII may be of any length that is allowable by the molecular marker assay suitably used for identifying the markers disclosed herein, and therewith identifying QTL-XII. In an embodiment of the current invention, the marker for identification of QTL-VI comprises a sequence selected from the group of SEQ ID NO: 5, SEQ ID NO: 6, SEQ ID NO: 7 and SEQ ID NO: 8.

In a preferred embodiment, the invention relates to one or more markers as described herein for identification of QTL-VI and one or more markers as described herein for identification of QTL-XII. The invention also relates to one or more markers as described herein for identification of QTL-VI in combination with one or more markers as described herein for identification of QTL-XII.

As indicated above, the location of QTL-VI on chromosome 6 is within the chromosomal region delimited by SEQ ID NO: 1 and SEQ ID NO: 2, preferably within the chromosomal region delimited by SEQ ID NO: 3 and SEQ ID NO: 4, as comprised in a melon plant representative seed of which was deposited with the NCIMB under deposit numbers NCIMB 42991. Thus, melon accession NCIMB 42991 represent the natural genetic background of the QTLs of the invention.

The nucleic acid sequence of QTL-VI of the present invention may be determined by methods known to the skilled person. For instance, a nucleic acid sequence comprising QTL-VI or a resistance-conferring part or variant thereof may be isolated from a donor plant. This may for example be done by fragmenting the genome of said plant and selecting fragments comprising one or more markers indicative of QTL-VI, for example comprising the markers represented by any of SEQ ID NO: 1-4, or a combination of at least two thereof. For example markers represented by SEQ ID NO 1 and SEQ ID NO 2, or SED NO 3 and 4. The marker sequences may also be used as amplification primers to amplify a nucleic acid sequence comprising QTL-VI. The amplified sequence may then be purified as to obtain the isolated QTL-VI, or part or variant thereof. The nucleotide sequence of QTL-VI, may then be obtained by standard sequencing methods well-known to the skilled person.

Therefore, in an embodiment of the invention there is provided for an (isolated) nucleic acid (or construct) comprising QTL-VI, or a part or variant thereof leading to powdery mildew resistance, as comprised in the genome of NCIMB 42991 located on chromosome 6 within the chromosomal region delimited by SEQ ID NO: 1 and SEQ ID NO: 2, preferably within the region delimited by SEQ ID NO: 3 and SEQ ID NO: 4.

In other words, also provided is for an isolated nucleic acid, or vector or construct comprising such nucleic acid, that comprises QTL-VI of the present invention, or a powdery mildew resistance conferring part or variant thereof. Thus, the markers for QTL-VI as described herein may be used for the identification and isolation of one or more gene comprised in QTL-VI and that confer powdery mildew resistance.

As indicated above, the location of QTL-XII on chromosome 12 is within the chromosomal region delimited by SEQ ID NO: 5 and SEQ ID NO: 6, preferably within the chromosomal region delimited by SEQ ID NO: 7 and SEQ ID NO: 8, as comprised in a melon plant representative seed of which was deposited with the NCIMB under deposit numbers NCIMB 42991 Thus, melon accession NCIMB 42991 represent the natural genetic background of the QTLs, including QTL-XII, of the invention.

The nucleic acid sequence of QTL-XII of the present invention may be determined in an analogous manner as described above for QTL-VI.

Therefore, in an embodiment of the invention there is provided for an (isolated) nucleic acid (or construct) comprising QTL-XII, or a part or variant thereof leading to powdery mildew resistance when present in a plant further comprising QTL-VII preferably in homozygous form, as comprised in the genome of NCIMB 42991 located on chromosome 12 within the chromosomal region delimited by SEQ ID NO: 5 and SEQ ID NO: 6, preferably within the region delimited by SEQ ID NO: 7 and SEQ ID NO: 8.

In other words, also provided is for an isolated nucleic acid, or vector or construct comprising such nucleic acid that comprises QTL-XII of the present invention, or a powdery mildew resistance conferring part or variant thereof. Thus, the markers for QTL-XII as described herein may be used for the identification and isolation of one or more genes comprised in QTL-XII and that confer powdery mildew resistance, in particular in combination with QTL-VI or one or more genes comprised in QTL-VI and that confer powdery mildew resistance.

A part or variant of QTL-VI, is to be understood herein is a part or variant that is capable of conferring powdery mildew resistance substantially to the extend as QTL-VI, wherein said part or variant preferably comprises a sequence that has at least 60%, 70%, 80%, 90%, 95%, 96%, 97%, 98% or 99% sequence identity to QTL-VI. Similarly, a part or variant of QTL-XII, is to be understood herein is a part or variant that is capable of conferring powdery mildew resistance substantially to the extend as QTL-VI, wherein said part or variant preferably comprises a sequence that has at least 60%, 70%, 80%, 90%, 95%, 96%, 97%, 98% or 99% sequence identity to QTL-XII.

Optionally, a nucleic acid, vector or construct or construct of the invention may be non-naturally occurring, e.g. comprise sequences that are not operably linked in nature. For instance, such nucleic acid, vector or construct may be a probe for detection comprising at least one marker as defined herein and a non-naturally occurring primer binding sequence and/or a sequence for barcoding or indexing which aids in the detection. The nucleic acid, vector or construct may also be for expression and comprising one or more of the QTL-VI, or part or variant thereof as defined herein for conferring powdery mildew resistance, and/or QTL-XII, or part or variant thereof as defined herein for conferring powdery mildew resistance, operably linked to a non-native promoter, i.e. a promoter sequence that is not normally operably linked to said QTL. Optionally, said construct comprises both QTL-VI, or part or variant thereof as defined herein for conferring powdery mildew resistance, and QTL-XII, or part or variant thereof as defined herein for conferring powdery mildew resistance.

Said promoter preferably is a promoter suitable for expression in a plant cell, preferably in a plant of the species *Cucumis melo*. The promoter for expression in plant cells can be a constitutive promoter, an inducible promoter or a tissue specific promoter. Preferably, the promoter is a constitutive promoter.

As explained above, the markers as described herein for the identification of QTL-VI are in particular useful for identifying the presence of QTL-VI in the genome of a plant of the species *Cucumis melo*. Therefore, an embodiment of the invention relates to use of a marker of QTL-VI as described herein for identification of a QTL-VI in the genome of a plant of the species *Cucumis melo*.

As explained above, the markers as described herein for the identification of QTL-XII are in particular useful for identifying the presence of QTL-XII in the genome of a plant of the species *Cucumis melo*. Therefore, an embodiment of the invention relates to use of a marker of QTL-XII as described herein for identification of a QTL-XII in the genome of a plant of the species *Cucumis melo*.

As the skilled person will understand, the markers identified herein for QTL-VI and/or QTL-XII can be used to indicate the presence of QTL-VI and/or QTL-XII (and thus of the associated powdery mildew resistance phenotype). The combination of markers identified herein for QTL-VI and QTL-XII can be used to indicate the presence of the combination of QTL-VI and QTL-XII. This can be done in an individual plant or in many plants, and as such they can be used in marker assisted selection (MAS) procedures, for example in breeding programs aimed at providing plants of the species *Cucumis melo* with improved resistance to powdery mildew resistance.

It is contemplated that any marker that is linked to the QTL, e.g. falling within the delimitation of the genomic region between the respective markers for the QTLs, may be used in marker-assisted selection.

Because reliable and reproducible phenotypical assays for establishing powdery mildew infection are time consuming, the use of markers linked to the QTL identified herein are desirable in breeding for powdery mildew resistance in plants of the species *Cucumis melo*. As will be understood by the skilled person, marker-assisted selection may be performed using known methods, including methods using the markers as described herein.

Therefore, an embodiment of the invention relates to a method for selecting a powdery mildew resistant plant, preferably of the species *Cucumis melo*, wherein the method comprises detecting the presence of at least one marker as described herein for QTL-VI, and optionally further comprising detecting the presence of at least one marker as described herein for QTL-XII. Preferably, selected is for a plant comprising QTL-VI in a homozygous form, optionally in combination with QTL-XII being present in heterozygous or homozygous form.

In a further embodiment, the invention relates to a method for selecting a plant with increased powdery mildew resistance, preferably a plant of the species *Cucumis melo*, wherein the method comprises detecting the presence of at least one marker as described herein for QTL-XII. The selection may be for a plant comprising QTL-XII in heterozygous or homozygous form. Increased powdery mildew resistance of a plant comprising QTL-XII is to be understood herein as scoring at least 1, 1.5, 2, 2.5 or 3 points lower in the bioassay as compared to a control plant not bearing QTL-XII, wherein preferably said plant and control plant both comprise QTL-VI as defined herein.

Another embodiment of the invention relates to a method of producing a powdery mildew resistant plant of the species *Cucumis melo*, wherein the method comprises introducing into a plant QTL-VI as comprised in the genome of NCIMB 42991 located on chromosome 6 within the chromosomal region delimited by SEQ ID NO: 1 and SEQ ID NO: 2, preferably within the region delimited by SEQ ID NO: 3 and SEQ ID NO: 4, optionally in combination with introducing into the plant QTL-XII as comprised in the genome of NCIMB 42991 located on chromosome 6 within the chromosomal region delimited by SEQ ID NO: 5 and SEQ ID NO: 6, preferably within the region delimited by SEQ ID NO: 7 and SEQ ID NO: 8.

Another embodiment of the invention relates to a method of producing a plant having increased powdery mildew resistance, wherein the method comprises introducing into a plant QTL-XII as comprised in the genome of NCIMB 42991 located on chromosome 12 within the chromosomal region delimited by SEQ ID NO: 5 and SEQ ID NO: 6, preferably within the chromosomal region delimited by SEQ ID NO: 7 and SEQ ID NO: 8.

Introduction of QTL-VI and/or QTL-XII, or an isolated nucleic acid comprising QTL-VI and/or QTL-XII, or a powdery mildew resistance-conferring part or variant thereof, into a another plant, preferably a plant of the species *Cucumis melo*, even more preferably a plant of the species *Cucumis melo* that is susceptible for powdery mildew infection, may be performed by any method known to the skilled person. In one embodiment, the powdery mildew resistant plant, preferably of the species *Cucumis melo*, is produced by introduction of QTL-VI and/or QTL-XII, or a powdery mildew resistance-conferring part or variant thereof, by introgression (crossing). Introgression may be performed by crossing of a plant of melon accession NCIMB 42991, or any other plant of the species *Cucumis melo* that comprises QTL-VI and/or QTL-XII or part or variant thereof as detailed herein, or a powdery mildew resistance-conferring part or variant thereof, with a powdery mildew susceptible plant, preferably with a plant of the species *Cucumis melo* not comprising QTL-VI and/or QTL-XII or a powdery mildew resistance-conferring part or variant thereof. The skilled person is well aware of suitable methods of crossing/introgressing in accordance with the invention described herein. In some embodiments, for example, the resulting plant population from the initial cross (representing the F1 population) may be self-pollinated and allowed to set seeds (F2 seeds). The F2 plants grown from the F2 seeds may then be screened for resistance for powdery mildew and/or for the presence of QTL-VI and/or QTL-XII or the markers for identification of QTL-VI and/or QTL-XII as described herein. The presence of the QTL-VI and/or QTL-XII in the progeny (e.g. F1 or F2, or later generations) may thus be confirmed by detecting the presence in the genome of said progeny a marker linked to QTL-VI and/or QTL-XII, preferably a marker as disclosed herein.

An embodiment of the invention relates to a method of producing a powdery mildew resistant plant of the species *Cucumis melo*, wherein the method comprises transferring into a plant, preferably a plant of the species *Cucumis melo* that is susceptible to powdery mildew infection, an (isolated) nucleic acid (or construct) comprising QTL-VI, or a part or variant thereof leading to powdery mildew resistance, as comprised in the genome of NCIMB 42991 located on chromosome 6 within the chromosomal region delimited by SEQ ID NO: 1 and SEQ ID NO: 2, preferably within the region delimited by SEQ ID NO: 3 and SEQ ID NO: 4, wherein said transferring is optionally performed by transformation, protoplast fusion, double haploid technique or embryo rescue. Preferably, the method results in the presence of QTL-VI in homozygous form.

The method also encompasses, alone or in combination with the afore mentioned embodiment, a method of producing a powdery mildew resistant plant of the species *Cucumis melo*, wherein the method comprises transferring into a plant, preferably a plant of the species *Cucumis melo* that is susceptible to powdery mildew infection, an (isolated) nucleic acid (or construct) comprising QTL-XII, or a part or variant thereof leading to powdery mildew resistance, as comprised in the genome of NCIMB 42991 located on chromosome 12 within the chromosomal region delimited by SEQ ID NO: 5 and SEQ ID NO: 6, preferably within the region delimited by SEQ ID NO: 7 and SEQ ID NO: 8, wherein said transferring is optionally performed by transformation, protoplast fusion, double haploid technique or embryo rescue. Preferably, the method results in the presence of QTL-XII in heterozygous or homozygous form. The method may further comprise the step of transferring into the plant QTL-VI as detailed herein, preferably in homozygous form.

The method also encompasses a method of producing a powdery mildew resistant plant of the species *Cucumis melo*, wherein the method comprises transferring into a plant, preferably a plant of the species *Cucumis melo* that is susceptible to powdery mildew infection, an (isolated) nucleic acid (or construct) comprising both QTL-VI, or a part or variant thereof leading to powdery mildew resistance, and QTL-XII, or a part or variant thereof leading to powdery mildew resistance, wherein QTL-VI is as comprised in the genome of NCIMB 42991 located on chromosome 6 within the chromosomal region delimited by SEQ ID NO: 1 and SEQ ID NO: 2, preferably within the region delimited by SEQ ID NO: 3 and SEQ ID NO: 4, and wherein QTL-XII is as comprised in the genome of NCIMB 42991 located on chromosome 12 within the chromosomal region delimited by SEQ ID NO: 5 and SEQ ID NO: 6, preferably within the region delimited by SEQ ID NO: 7 and SEQ ID NO: 8, wherein said transferring is optionally performed by transformation, protoplast fusion, double haploid technique or embryo rescue. Preferably, the method results in the presence of QTL-VI in homozygous form and the presence of QTL-XII in heterozygous or homozygous form.

As described herein, QTL-VI and QTL-XII were first recognized in melon accession NCIMB 42991, but, as the skilled person will be aware, any other plant of the species *Cucumis melo* that comprises QTL-VI and/or QTL-XII, or a powdery mildew resistance-conferring part or variant thereof, and as can be identified using the markers as described herein, may be used for isolation of the nucleic acid and/or preparing a construct comprising QTL-VI and/or QTL-XII, or a part or variant thereof leading to powdery mildew resistance. Once isolated, the QTL-VI and/or QTL-XII or powdery mildew resistance conferring part or variant thereof may be transferred into a suitable plant or organism by any method available to the skilled person. Preferably, said plant is susceptible to powdery mildew infection, preferably a plant of the species *Cucumis melo*.

It is however important to note that in some embodiments, both relating to the introgression as described above and/or relating to the transfer of an (isolated) nucleic acid (or construct) comprising QTL-VI and/or QTL-XII, or a part or variant thereof leading to powdery mildew resistance, using genetic means (i.e. not involving crossing), the acceptor plant may be a plant already comprising other genes or QTLs related to powdery mildew resistance. In such embodiments, several independent or interdependent genetic regions linked to powdery mildew resistance are combined in one and the same plant in order to increase resistance to powdery mildew infection.

As mentioned, transferring of an isolated nucleic acid comprising QTL-VI and/or QTL-XII, or a part or variant thereof leading to powdery mildew resistance, into a melon plant may be performed by any method known to the skilled person. Non-limiting examples of such methods include transformation and protoplast fusion. However any other suitable nucleic acid transfer system may be used. In some embodiments, the transferring is followed by selection of off-spring plants comprising the QTL-VI and/or QTL-XII, or powdery mildew conferring part or variant thereof. Transfer may be performed using plant cells. For some methods the isolated nucleic acid may be transferred to the recipient plant for instance by means of a vector, in a gamete, or in any other suitable transfer element. One well-known method for introducing an expression vector into a plant is based on the transformation system of *Agrobacterium* (see e.g. Horsch et al., 1985).

Also provided is a powdery mildew resistant *Cucumis melo* plant comprising introgressed in its genome QTL-VI as comprised in the genome of NCIMB 42991 on chromosome 6 within the chromosomal region delimited by SEQ ID NO: 1 and SEQ ID NO: 2, preferably delimited by SEQ ID NO: 3 and SEQ ID NO: 4. Preferably, said plant is a cultivar, more preferably a *Cucumis melo* subsp. *melo* cultivar from several botanical varieties, e.g. Vedrantais (var. *cantalupensis*), Piel de Sapo (var. *inodorus*) and *Dulce* (var. *reticulatus*).

Also provided is the powdery mildew resistant *Cucumis melo* plant described above, wherein the plant further comprises introgressed in its genome QTL-XII as comprised in the genome of NCIMB 42991 on chromosome 12 within the chromosomal region delimited by SEQ ID NO: 5 and SEQ ID NO: 6, preferably delimited by SEQ ID NO: 7 and SEQ ID NO: 8. The invention therefore also provides a powdery mildew resistant *Cucumis melo* plant, wherein the plant comprises introgressed in its genome both QTL-VI as comprised in the genome of NCIMB 42991 on chromosome 6 within the chromosomal region delimited by SEQ ID NO: 1 and SEQ ID NO: 2, preferably delimited by SEQ ID NO: 3 and SEQ ID NO: 4, and QTL-XII as comprised in the genome of NCIMB 42991 on chromosome 12 within the chromosomal region delimited by SEQ ID NO: 5 and SEQ ID NO: 6, preferably delimited by SEQ ID NO: 7 and SEQ ID NO: 8. Preferably, said plant is a cultivar, more preferably a *Cucumis melo* subsp. *melo* cultivar from several botanical varieties, e.g. Vedrantais (var. *cantalupensis*), Piel de Sapo (var. *inodorus*) and *Dulce* (var. *reticulatus*), Also provided is a powdery mildew resistant *Cucumis melo* plant comprising introgressed in its genome QTL-XII as comprised in the genome of NCIMB 42991 on chromosome 12 within the chromosomal region delimited by SEQ ID NO: 5 and SEQ ID NO: 6, preferably delimited by SEQ ID NO: 7 and SEQ ID NO: 8. Preferably, said plant is a cultivar, more preferably a *Cucumis melo* subsp. *melo* cultivar from several botanical varieties, e.g. Vedrantais (var. *cantalupensis*), Piel de Sapo (var. *inodorus*) and *Dulce* (var. *reticulatus*).

Finally there is provided for a marker as described herein, an (isolated) nucleic acid as described herein, use as described herein, or a method or plant as described herein, wherein the powdery mildew causal agent is the fungus *Podosphaera xanthii* in particular wherein the powdery mildew causal agent is the fungus *Podosphaera xanthii* race 3.5 (S13.5) (M. Pitrat and D. Besombes. Inheritance of *Podosphaera xanthii* resistance in melon line '90625'.Cucurbitaceae 2008, Proceedings of the IXth EUCARPIA meeting on genetics and breeding of Cucurbitaceae (Pitrat M, ed), INRA, Avignon (France), May 21-24th, 2008: 135-142), even more in particular, Sf3.5A or Sf3.5B.

Considering the benefits of the present plants, i.e., providing powdery mildew resistance in melon plants, the invention also relates to seeds, plant parts or propagation material capable of providing the present powdery mildew resistant melon plants which seeds, plant parts or propagation material comprise one or more of the present powdery mildew resistance QTLs, or parts thereof, as described herein. The invention also relates to non-propagating material derived from powdery mildew resistance melon plants, seed or plant parts of the present invention, i.e. beverage, juice, protein, sugar and the like. Preferably, said propagating material and/or non-propagating material is characterized in that it comprises QTL-VI and/or QTL-XII as defined herein, or part or variant thereof conferring powdery mildew resistance. Optionally, said propagating material and/or non-propagating material is characterized in that it comprises non naturally occurring sequences comprising QTL-VI and/or QTL-XII as defined herein The invention also relates to the use of a plant of the invention that comprises QTL-VI, QTL-XII or a combination of QTL-VI and QTL-XII as a source of propagating material. The invention also relates to the use of a plant of the invention that comprises QTL-VI, QTL-XII or a combination of QTL-VI and QTL-XII in plant breeding.

The invention also relates to a cell of a plant as claimed. Such cell comprises or is provided with the genetic information (QTL-VI and/or QTL-XII, or powdery mildew conferring part(s) thereof) that leads to resistance to powdery mildew. The invention also relates to progeny of the plants, cells, tissues and seeds of the invention.

It will be understood that all details, embodiments and preferences discussed with respect to one aspect of embodiment of the invention is likewise applicable to any other aspect or embodiment of the invention and that there is therefore not need to detail all such details, embodiments and preferences for all aspect separately.

Having now generally described the invention, the same will be more readily understood through reference to the following examples which is provided by way of illustration and is not intended to be limiting of the present invention.

EXAMPLES

Examples

Sf3.5A and Sf3.5B Multiplication

Detached cotyledons of 8-10 days old melon Vedrantais were used for Sf3.5A or Sf3.5B multiplication. After 10 days these inoculated cotyledons were used for inoculation.

Phenotyping of Resistance to Powdery Mildew (Sf3.5A and Sf3.5B)

Seeds to be tested were sown in plastic trays filled with turf and grown in the glasshouse until 3 leave stage. Subsequently, the plants were inoculated using the inoculated cotyledons of melon Vedrantais by putting the plastic trays with the plants to be tested on the floor of a clean room and gently blowing the spores of the Sf3.5A or Sf3.5B inoculated cotyledons of melon Vedrantais at the top with an air compressor. The concentration of the spores was between 100 to 400 spores/cm$^2$. Subsequently, the plastic trays with the plants were put in a climate cell at 20° C. with 12 h light for 10 to 12 days. After this incubation period of 10 to 12 days, the plants were phenotyped for resistance. For phenotyping, one leaf disc per plant is sampled from the youngest leave of the plant. Resistance was scored according to Table 1. FIG. 1 exemplifies leaf discs, which were recorded as Resistance Score 3, 4, 6 and 8, respectively.

TABLE 1

Observation and interpretation for resistance scoring.

| Resistance Score | Observation | Interpretation |
|---|---|---|
| 1 | No visual changes | Resistant with a very good level |
| 2 | Some isolated spots, with low sporulation (<10% surface) visible on the edges. | Resistant |
| 3 | Some more slightly sporulating spots visible, mainly along the veins (<25 to 50% surface) | Intermediate |
| 4 | Low sporulation becoming apparent | Slightly susceptible |
| 5-6 | Apparent sporulation (Slightly white) | Susceptible |
| 7-8 | Medium sporulation (white) | |
| 9 | Strong sporulation (very white) | |

Resistance Scoring of Introgressed Phenotyping of Resistance to Powdery Mildew (Sf3.5A and Sf3.58)

F3 plants, derived from selected RILs (recombinant inbred lines, deposited under NCIMB 42991), were phenotyped for powdery mildew resistance. Powdery mildew resistance was scored in two replications for two strains Sf3.5 (Sf3.5A and Sf3.58). At the first replication, 2649 F3 plants were tested for Sf3.5A resistance and 2654 F3 plants were tested for Sf3.58 resistance. At the second replication, 1952 F3 plants were tested for Sf3.5A resistance and 1961 F3 plants were tested for Sf3.58 resistance. Genotyping on these plants was performed on the day of phenotyping, using the markers represented by SEQ ID NO: 3 and 4 for QTL-VI and SEQ ID NO: 7 and 8 for QTL-XII, wherein the presence of these markers identifies the presence of the resistant allele of these QTLs derived from NCIMB 42991. The number of observations per combined QTL genotype class is given in Table 2.

TABLE 2

Number of observations per combined QTL genotype class (A is homozygous for QTL-VI or QTL-XII of susceptible melon strain Vedrantais, B is homozygous for QTL-VI or QTL-XII of resistant melon strain NCIMB 42991, H is heterozygous for QTL-VI or QTL-XII of susceptible melon strains Vedrantais and resistant melon strain NCIMB 42991.

| Genotype | | |
|---|---|---|
| QTL-VI | QTL-XII | # observations |
| A | A | 4 |
| B | A | 585 |
| H | A | 0 |
| A | B | 654 |
| B | B | 872 |
| H | B | 194 |
| A | H | 0 |
| B | H | 137 |
| H | H | 0 |

Figure 2:
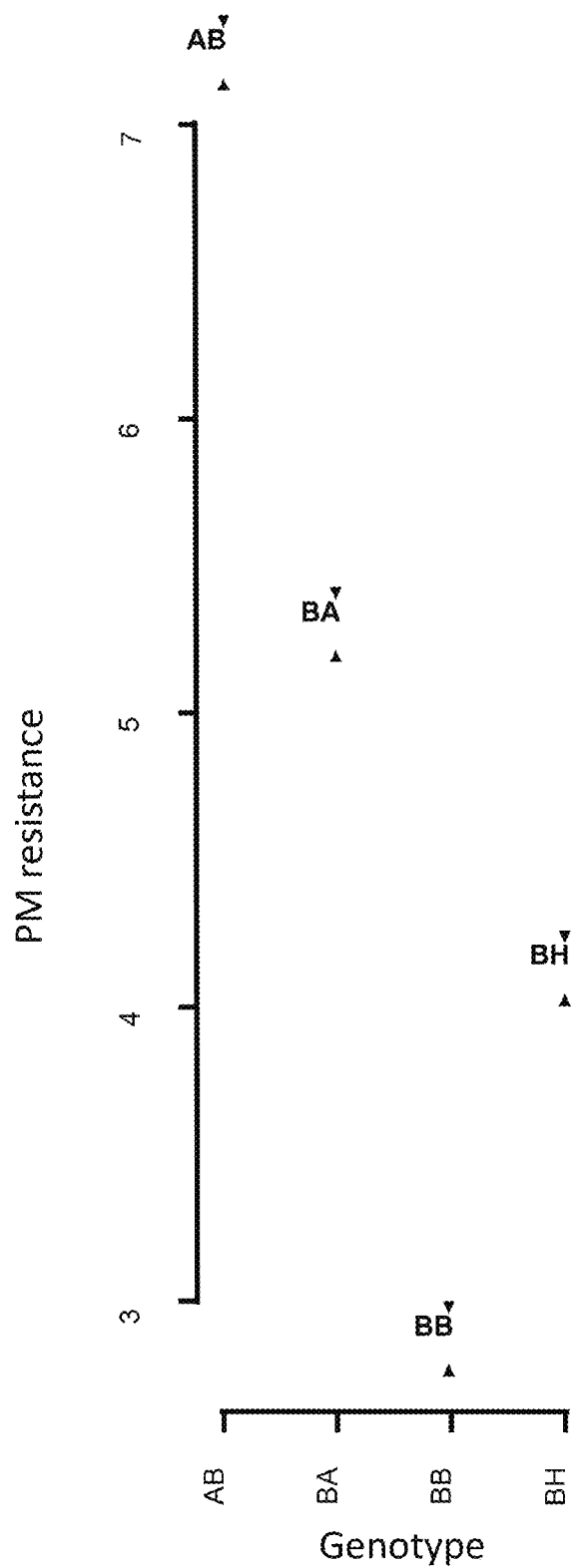
FIG. 2: Correlation between genotype and phenotype (95% confidence regions).

The 95% confidence regions was determined for the correlations between the genotype and phenotype (LOD-drop 2, Baysian confidence interval and Bootstrap confidence interval). The results of genotypes BA, AB, BB and BH (first letter relating to the genotype of QTL-VI according to Table 2, second letter relating to the genotype of QTL-XII according to Table 2) correlated to the scored Sf3.58 resistance is presented in FIG. 2. Genotype HB resulted in a susceptible phenotype comparable to genotype AB (data not shown). Similar results were obtained for resistance to Sf3.5A (data not shown).

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding patent applications, patents, or any other references, are entirely incorporated by reference herein, including all data, tables, figures, and text presented in the cited references. Additionally, the entire contents of the references cited within the references cited herein are also entirely incorporated by references. Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

The invention claimed is:

1. A powdery mildew resistant *Cucumis melo* plant, comprising introgressed or transferred in its genome:
   (i) QTL-VI as comprised in the genome of NCIMB 42991 on chromosome 6 within the chromosomal region delimited by SEQ ID NO: 1 and SEQ ID NO: 2; and
   (ii) QTL-XII as comprised in the genome of NCIMB 42991 on chromosome 12 within the chromosomal region delimited by SEQ ID NO: 5 and SEQ ID NO: 6.

2. The powdery mildew resistant *Cucumis melo* plant of claim 1, wherein the 'G' on position 23 of SEQ ID NO: 1 corresponds to the physical position 5,330,645 bp of the public melon genome and/or the 'A' on position 23 of SEQ ID NO: 2 corresponds to the physical position 6,006,456 bp of the public melon genome.

3. The powdery mildew resistant *Cucumis melo* plant of claim 1, wherein the powdery mildew resistant plant comprises at least one marker, having at least one of:
   (a) 'G' on position 23 of SEQ ID NO: 1 corresponding to the physical position 5,330,645 bp of the public melon genome;
   (b) 'A' on position 23 of SEQ ID NO: 2 corresponding to the physical position 6,006,456 bp of the public melon genome; and
   (c) SEQ ID NO: 1 or SEQ ID NO: 2.

4. The powdery mildew resistant *Cucumis melo* plant of claim 1, comprising introgressed or transferred in its genome QTL-VI as comprised in the genome of NCIMB 42991 on chromosome 6 within the chromosomal region delimited by SEQ ID NO: 3 and SEQ ID NO: 4.

5. The powdery mildew resistant *Cucumis melo* plant of claim 4, wherein the 'T' on position 23 of SEQ ID NO: 3 corresponds to the physical position 5,414,506 bp of the public melon genome, and/or the 'C' on position 23 of SEQ ID NO: 4 corresponds to the physical position 5,738,920 bp of the public melon genome.

6. The powdery mildew resistant *Cucumis melo* plant of claim 5, wherein the powdery mildew resistant plant comprises at least one marker, having at least one of:
   (a) 'T' on position 23 of SEQ ID NO: 3 corresponding to the physical position 5,414,506 bp of the public melon genome;
   (b) 'C' on position 23 of SEQ ID NO: 4 corresponding to the physical position 5,738,920 bp of the public melon genome; and
   (c) SEQ ID NO: 3 or SEQ ID NO: 4.

7. The powdery mildew resistant *Cucumis melo* plant according to claim 1, wherein the plant is a cultivar.

8. The powdery mildew resistant *Cucumis melo* plant of claim 1, wherein the 'T' on position 23 of SEQ ID NO: 5 corresponds to the physical position 22,675,877 bp of the public melon genome and/or the 'T' on position 23 of SEQ ID NO: 6 corresponds to the physical position 22,923,842 bp of the public melon genome.

9. The powdery mildew resistant *Cucumis melo* plant of claim 1, wherein the powdery mildew resistant plant comprises at least one marker having at least one of:
   (a) 'T' on position 23 of SEQ ID NO: 5 corresponding to the physical position 22,675,877 bp of the public melon genome;
   (b) 'T' on position 23 of SEQ ID NO: 6 corresponding to the physical position 22,923,842 bp of the public melon genome; and
   (c) SEQ ID NO: 5 or SEQ ID NO: 6.

10. The powdery mildew resistant *Cucumis melo* plant according to claim 1, wherein the QTL-XII as comprised in the genome of NCIMB 42991 on chromosome 12 is within the chromosomal region delimited by SEQ ID NO: 7 and SEQ ID NO: 8.

11. The powdery mildew resistant *Cucumis melo* plant of claim 10, wherein the 'C' on position 23 of SEQ ID NO: 7 corresponding to the physical position 22,781,889 bp of the public melon genome, and the 'G' on position 23 of SEQ ID NO: 8 corresponding to the physical position 22,788,588 bp of the public melon genome.

12. The powdery mildew resistant *Cucumis melo* plant of claim 10, wherein the powdery mildew resistant plant comprises at least one marker having at least one of:
 (a) 'C' on position 23 of SEQ ID NO: 7 corresponding to the physical position 22,781,889 bp of the public melon genome;
 (b) 'G' on position 23 of SEQ ID NO: 8 corresponding to the physical position 22,788,588 bp of the public melon genome; and
 (c) SEQ ID NO: 7 or SEQ ID NO: 8.

13. The powdery mildew resistant *Cucumis melo* plant according to claim 1, wherein the powdery mildew causal agent is the fungus *Podosphaera xanthii*.

* * * * *